(12) United States Patent
Zada

(10) Patent No.: US 9,033,974 B2
(45) Date of Patent: May 19, 2015

(54) MULTI-FUNCTIONAL SURGICAL CAUTERY DEVICE, SYSTEM AND METHOD OF USE

(71) Applicant: Gabriel Zada, Los Angeles, CA (US)

(72) Inventor: Gabriel Zada, Los Angeles, CA (US)

(*) Notice: Subject to any disclaimer, the term of this patent is extended or adjusted under 35 U.S.C. 154(b) by 0 days.

(21) Appl. No.: 14/508,924

(22) Filed: Oct. 7, 2014

(65) Prior Publication Data
US 2015/0025530 A1  Jan. 22, 2015

Related U.S. Application Data

(63) Continuation of application No. 13/922,000, filed on Jun. 19, 2013.

(60) Provisional application No. 61/661,459, filed on Jun. 19, 2012.

(51) Int. Cl.
| | |
|---|---|
| A61B 18/14 | (2006.01) |
| A61B 18/08 | (2006.01) |
| A61B 18/00 | (2006.01) |
| A61B 19/00 | (2006.01) |

(52) U.S. Cl.
CPC ................. *A61B 18/14* (2013.01); *A61B 18/08* (2013.01); *A61B 18/00* (2013.01); *A61B 18/1445* (2013.01); *A61B 19/2203* (2013.01); *A61B 2018/00595* (2013.01); *A61B 2018/146* (2013.01); *A61B 2018/1462* (2013.01); *A61B 2218/007* (2013.01); *A61B 2018/00077* (2013.01); *A61B 2018/00321* (2013.01); *A61B 2018/00327* (2013.01); *A61B 2018/1452* (2013.01); *A61B 2218/002* (2013.01)

(58) Field of Classification Search
CPC ............ A61B 2018/00434; A61B 2018/00446
USPC ........................................................ 606/50–52
See application file for complete search history.

(56) References Cited

U.S. PATENT DOCUMENTS

| | | | |
|---|---|---|---|
| 5,376,094 A * | 12/1994 | Kline ............................ | 606/113 |
| 6,241,725 B1 | 6/2001 | Cosman | |
| 6,264,651 B1 * | 7/2001 | Underwood et al. .......... | 606/32 |
| 8,182,476 B2 | 5/2012 | Julian et al. | |
| 2001/0014806 A1 * | 8/2001 | Ellman et al. .................. | 606/45 |
| 2002/0111615 A1 | 8/2002 | Cosman et al. | |
| 2002/0188284 A1 * | 12/2002 | To et al. ......................... | 606/15 |
| 2002/0188294 A1 * | 12/2002 | Couture et al. ................ | 606/51 |

(Continued)

OTHER PUBLICATIONS

Cappabianca, Paolo. "Expanded Endoscopic Endonasal Approaches to the Skull Base." Cranial, Craniofacial and Skull Base Surgery. Milan: Springer, 2010. Print.*

*Primary Examiner* — Jaymi Della
(74) *Attorney, Agent, or Firm* — Knobbe Martens Olson & Bear LLP

(57) ABSTRACT

A surgical cautery device, system, and method of use may apply bipolar and/or sesquipolar electrocautery to target tissue via a pair of instruments with other primary surgical functions. The surgical cautery device and system may include first and second elements capable of forming an electrical circuit. The second element may be independently positionable with respect to the first element. The first and second elements may also include a surgical component with an independent surgical function. Exemplary surgical components include a rotary blade, a cutting tool, a grasper tool, a micro-scissors tool, a micro-grasping forceps tool, a dissector, a micro-dissector, curette, and a suction cannula. On some occasions, one of the surgical components may be interchangeable with another surgical component.

22 Claims, 7 Drawing Sheets

(56) References Cited

U.S. PATENT DOCUMENTS

| | | | |
|---|---|---|---|
| 2003/0130656 A1* | 7/2003 | Levin | 606/45 |
| 2003/0158545 A1* | 8/2003 | Hovda et al. | 606/32 |
| 2003/0171744 A1 | 9/2003 | Leung et al. | |
| 2006/0184161 A1* | 8/2006 | Maahs et al. | 606/2 |
| 2007/0066971 A1* | 3/2007 | Podhajsky | 606/34 |
| 2007/0156245 A1* | 7/2007 | Cauthen et al. | 623/17.16 |
| 2007/0260240 A1* | 11/2007 | Rusin | 606/45 |

\* cited by examiner

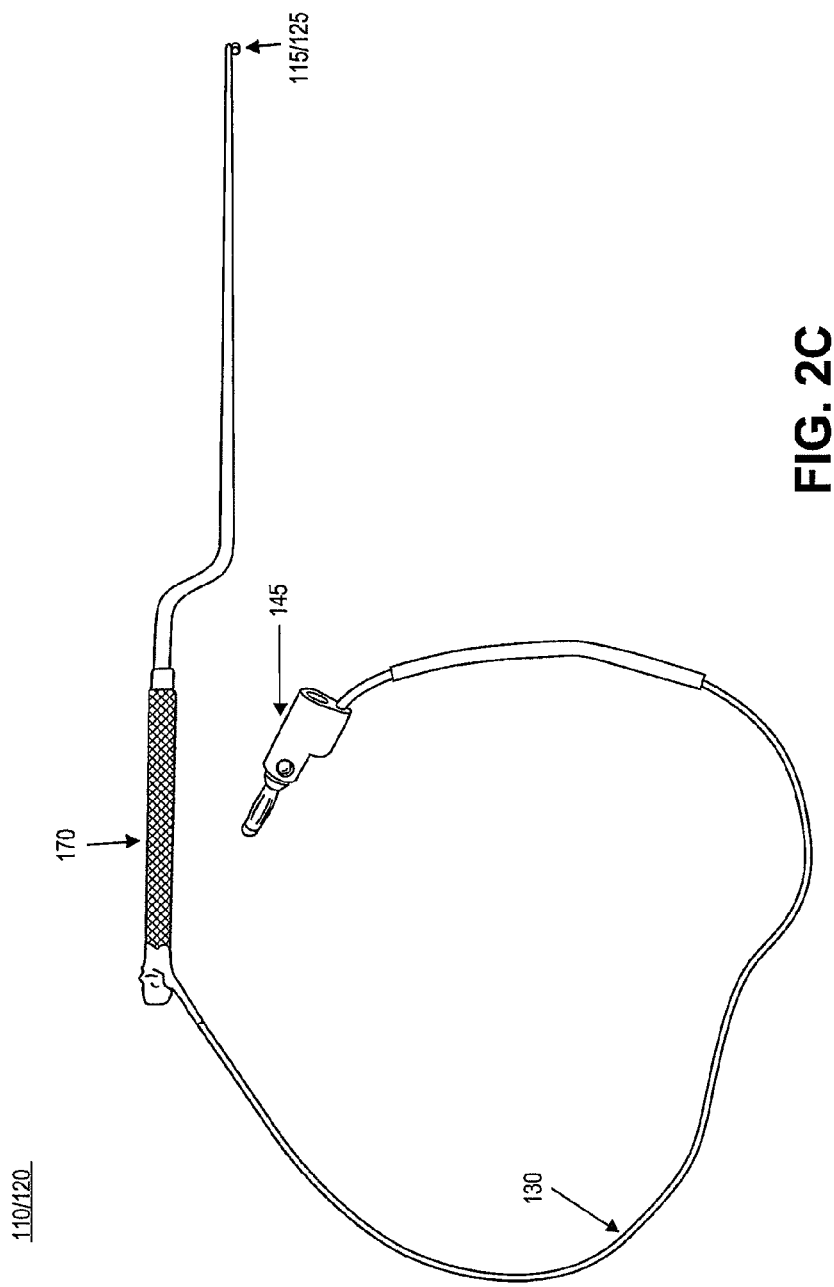

MULTI-FUNCTIONAL SURGICAL CAUTERY DEVICE, SYSTEM AND METHOD OF USE

RELATED APPLICATION

This application is a continuation of U.S. application Ser. No. 13/922,000, filed Jun. 19, 2013, which claims the benefit of U.S. Provisional Application No. 61/661,459, filed Jun. 19, 2012. The entireties of the above applications are incorporated by reference herein and are to be considered part of this specification.

TECHNICAL FIELD

The present invention relates to a surgical device, system, and method of use and, more particularly, to an endoscopic, minimally-invasive, multi-functional, modular cautery device, system, and method of use.

BACKGROUND

Endoscopic, minimally invasive, surgery relies on instrumentation for achieving hemostasis and surgical outcomes comparable to traditional open surgery techniques via comparatively small corridors, or ports, (e.g., nostrils or keyholes) within a patient. As yet, conventionally used bipolar cautery forceps have not been effectively translated into a functional instrument for use through the smaller corridors of this minimally invasive surgery. Presently used bipolar cauterization instruments suffer from limited mobility and visualization within the smaller corridors of minimally-invasive surgery and are difficult to use due to the relatively poor depth perception and stereoscopic vision offered within those corridors.

SUMMARY

A surgical cautery device, system, and method of use are herein described. The device is a modified method of applying bipolar and/or sesquipolar electrocautery to target tissue via a pair of instruments that retain other primary surgical functions. The device may include a first and second element. The second element may be independently positionable with respect to the first element. The first and second elements include a surgical component and may be capable of forming an electrical circuit. The surgical component may be made from an electrically conductive material, such as stainless steel. Exemplary surgical components include a cutting tool, rotary blade, grasper tool, micro-grasping forceps tool, ring curette, dissector or micro-dissector, micro-scissors tool, and a suction cannula, although a wide variety of insulated surgical instruments may be incorporated into this system. The surgical components are interchangeable, and can therefore be used in any combination to provide cautery application and increase efficiency of the operation. For example, when one surgical component is a suction cannula, it may be interchangeable with a cutting tool, a rotary blade, a grasper tool, a micro-scissors tool, a micro-grasping forceps tool, a dissector, a micro-dissector, or another suction cannula.

In many instances, the first and second elements are configured to contact a target tissue of a patient and, upon completion of the electrical circuit, deliver electrical energy to the target tissue. Often times, the delivery of the electrical energy to the target tissue acts to cauterize the target tissue.

Often times, a tip of the first and second elements may be electrically conductive while a portion of the first and second elements are electrically insulated from the tip. The first element and the second element may approach the target tissue through, for example, a conventional type of surgical opening, a single port (e.g., an endoscopic or microsurgery port), or a plurality of separate ports in the patient and may be configured to be manipulated by, for example, by a human surgeon and/or a robot.

Another exemplary device includes an electrically conductive wire that is electrically connected to an electrically insulated element. The electrically insulated element may include an electrically conductive surgical component. The surgical component may be capable of delivering electrical energy to a target tissue of a patient via the electrically conductive wire.

Exemplary systems consistent with embodiments of the present invention may include a source of electrical energy electrically coupled to the first and second elements. The second element may be independently positionable with respect to the first element. The first and second elements may have a surgical component and may be capable of forming an electrical circuit and delivering electrical energy from the source to a target tissue of a patient upon completion of the electrical circuit. The systems may deliver, for example, cautery, sesquipolar cautery, and/or bipolar cautery.

BRIEF DESCRIPTION OF THE DRAWINGS

The present invention is illustrated by way of example, and not limitation, in the figures of the accompanying drawings in which:

FIGS. 2A-2D depict exemplary first and/or second elements, consistent with embodiments of the present invention;

WRITTEN DESCRIPTION

Figure 1:
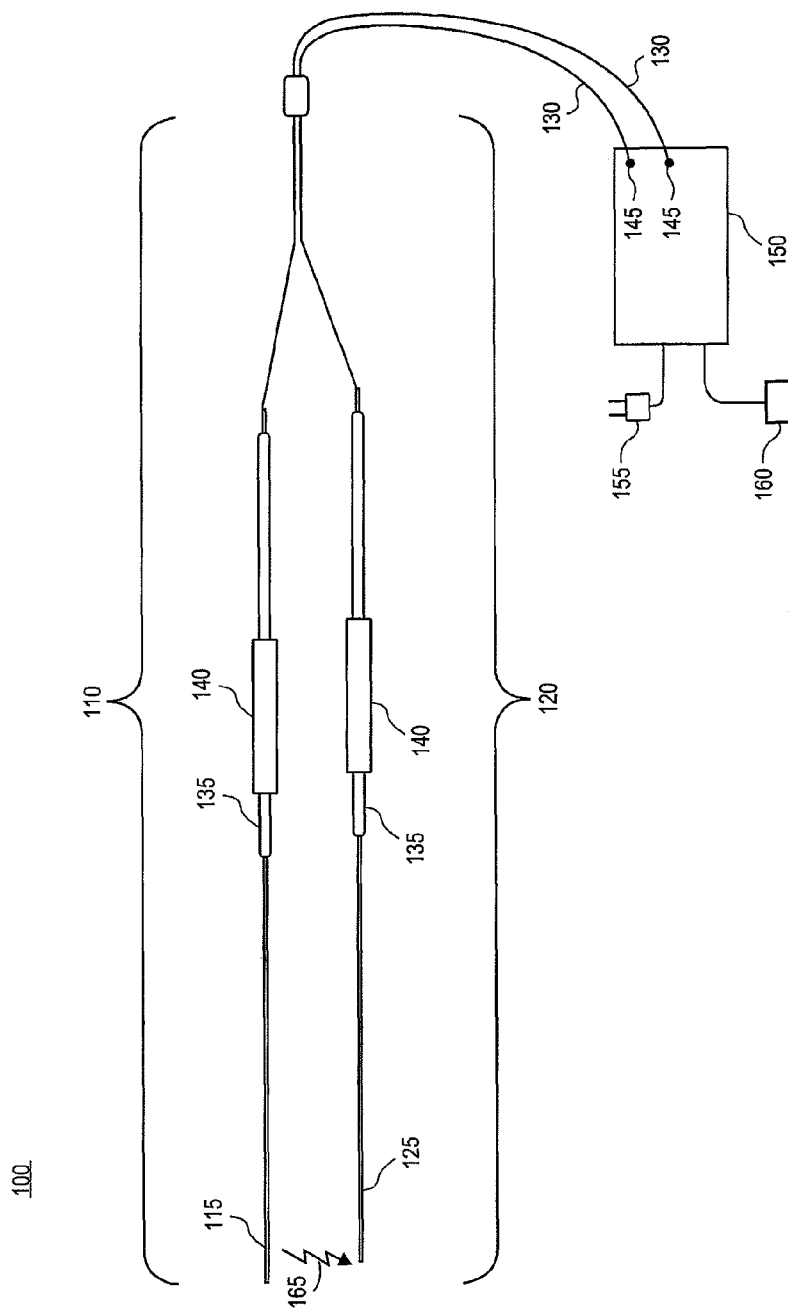
FIG. 1 depicts an exemplary surgical system, consistent with embodiments of the present invention.

Electrosurgical devices apply a high-frequency electric current to biological target tissue to cut, coagulate, or desiccate the target tissue or at least a portion of the target tissue. Electrosurgical devices use a generator (e.g., power supply or waveform generator) and a hand piece including one or several electrodes. Electrosurgery techniques are used in, for example, dermatological, gynecological, cardiac, plastic, ocular, spine, ear, nose, and throat (ENT), maxillofacial, orthopedic, urological, neuro- and general surgical procedures as well as certain dental procedures.

One of the benefits of modem endoscopic surgery is the ability to work through two or more ports, via a bimanual and/or robotic approach. Rather than constrain the size and mobility of a cautery device to one port, one embodiment of the current surgical system proposes a novel electrocautery technique, in which two separate "electrodes" of the system are also independently insulated modular devices with their own functional purpose (e.g., micro-grasping forceps, suction cannula, micro-scissors, dissectors, micro-dissectors, etc.). These dually-functioning components of the cautery system can manipulate target tissue with much greater mobility and visualization, and independently transmit opposing current from one electrode to another in order to achieve a sesquipolar or bipolar cautery effect (depending on, for example, the size and surface area of the conducting electrode surfaces) from one electrode to the other. Rather than functionally diverge near the tip of the forceps, as current models for endoscopic bipolar forceps propose, the current invention has two separate electrodes with dual function as another surgical device. The two electrodes diverge outside of the patient rather than within the surgical cavity, and are connected to each other and a power supply via wiring in order to appropriately transmit opposing high-frequency current to contacted target tissue. Each functional electrode/element of the electrocautery device may be insulated with respect to the surgical component, so that current will only be transmitted selectively from one surgical component to the other. The modular devices can be connected and disconnected to, for example, standard wires used with power supplies, such as bipolar electro cautery generators, and may be used in various combinations (e.g., suction cannula and micro-scissors or micro-grasping forceps and micro-scissors). Current may be activated via any conventionally available means, such as with a foot pedal in a manner similar to existing bipolar devices.

The present invention provides increased mobility and visualization in cauterizing the surgical target when compared with conventional techniques, by, for example, allowing two or more elements with surgical components to approach target tissue from different depths, angles, and/or ports. Each surgical component may have independent, interchangeable, and/or functional properties (i.e., cutting, grasping, dissection, sucking, probing, etc.), thus allowing a surgeon to manipulate delicate surgical target tissue as it is cauterized in an efficient manner. In addition, according to the present invention, the size of a surgical opening within a patient (i.e., port) need only accommodate one surgical component, which, in many cases, is smaller than traditionally used cauterizing forceps.

The present invention further allows a surgeon to perform surgical operations and cauterize with the same surgical components, thereby reducing the need to remove surgical devices from the patient and subsequently insert a separate cauterization device. Thus, utilization of the present invention increases surgical efficiency and potentially reduces the risk of infection or damage to surrounding anatomical structures that may be caused by repeatedly removing and inserting devices.

The present invention is more particularly described with regard to the exemplary embodiments depicted in the figures that accompany the instant patent application. For example, FIG. 1 depicts an exemplary surgical system 100 consistent with some embodiments of the present invention. Surgical system 100 may include a power supply 150, a power cord 155, and an activation device 160. Power supply 150 may be coupled to a first element 110 and a second element 120 via an electrical connector 145 (e.g., banana clip) electrically coupled to an electrically conductive wire 130. Power supply 150 may be any device capable of supplying electrical power, or current, to first and second elements 110 and 120 upon user selection of activation device 160. Activation device 160 may be any conventionally available means for initiating the delivery of electricity to first element 110 and/or second element 120 including, but not limited to, a foot petal, a button, or a dial. In some embodiments, an amount of power delivered to first and/or second elements 110 and 120 may be controlled by manipulation of activation device 160 (e.g., twisting a dial) in order to deliver a maximum level of power, or a fraction thereof, to first and/or second elements 110 and 120.

First and second elements 110 and 120 may be configured to deliver electrical energy 165 from power supply 150 to a contacted, or target, portion of tissue within a patient via surgical components 115 and/125. Exemplary target tissue includes a small blood vessel in need of cauterization, tumor, or other undesirable tissue to be removed from the patient. First and second elements 110 and 120 may be configured to be manipulated by a human surgeon and/or a robot and, on some occasions, may be configured to be used in microscopic or endoscopic single or multiple port surgery. In some embodiments, a portion of first and second elements 110 and 120, with the exception of a first and second surgical components 115 and 125, respectively, may be covered in electrical insulation 135 or may be otherwise insulated. In this way, only surgical components 115 and/or 125 may deliver electrical energy from power supply 150 to contacted tissue. Electrical insulation 135 may be any appropriate electrically insulating material including, but not limited to, plastic, vinyl, epoxy, parylene, or ceramic and may enable a surgeon to grasp and/or hold first and second elements 110 and 120 via, for example, graspers 140. First and/or second elements 110 and 120 as well as surgical components 115 and/or 125 may be disposable (i.e., one time use), or reusable (i.e., capable of being used multiple times).

On some occasions, first and second surgical components 115 and 125 may be similarly configured to one another with regard to shape and size and, in some instances, may comprise a matched pair of components. On other occasions, first surgical component 115 may be configured to perform a first function in addition to the conduction of electricity and second surgical component 125 may be configured to perform a second function in addition to the conduction of electricity. For example, first surgical component 115 may be configured to be operable by a robot while second surgical component 125 may be configured to be operable by a human surgeon. Additionally, one or both surgical components 115 and/or 125 may include one or more controls (not shown) that enable a manipulator of the surgical component (e.g., human surgeon or robot) to control the operation of the surgical component.

First and second elements 110 and 120 and/or first and second surgical components 115 and 125 may configured to be independently positionable by a human surgeon and/or a robot. In this way movement of, for example, first element 110 does not impact the position of second element 120. Likewise, on some occasions, movement of first surgical component 115 may not impact the position or functioning of second surgical component 125. In this manner, first and second elements 110 and 120 and/or first and second surgical components 115 and 125 may be moved independently within a patient and/or prior to entry into a patient to, for example, contact target tissue from different angles or enter different ports within a patient and/or perform different functions (in addition to the delivery of electricity) within the patient with regard to the target tissue.

Figure 2A:
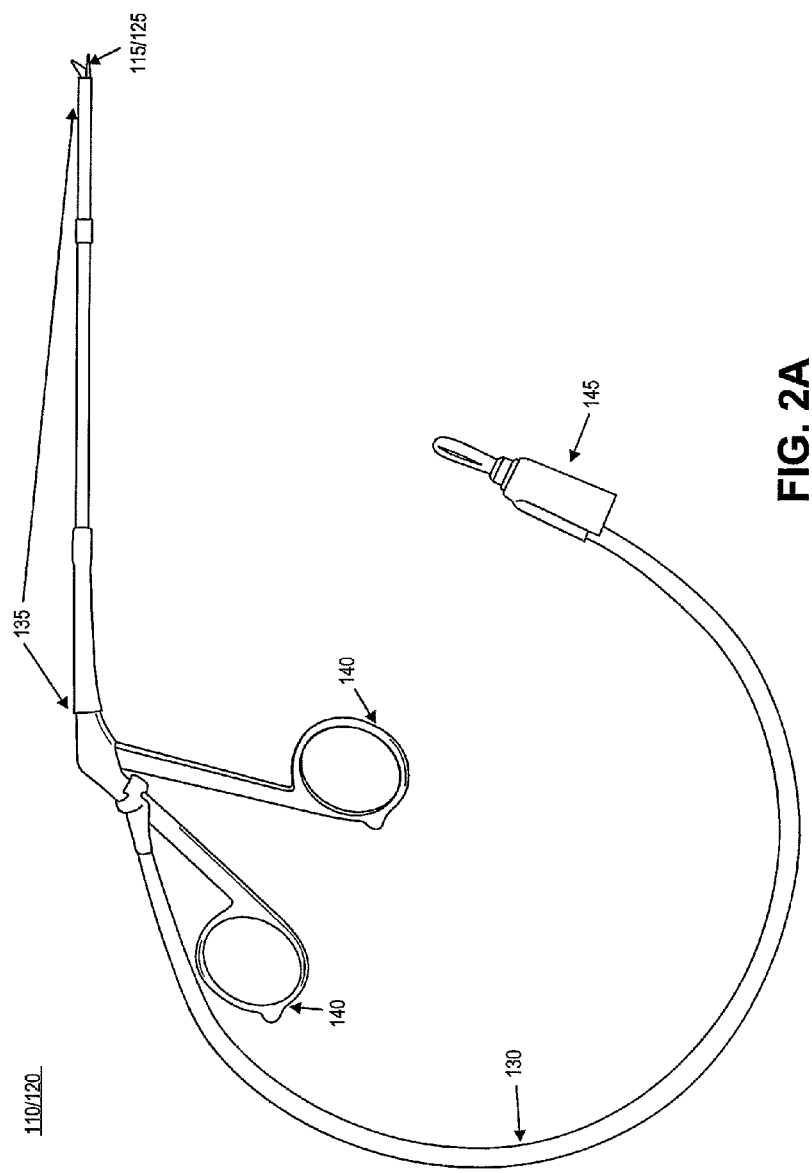

In some embodiments, first and second elements 115 and 125 may be interchangeable with other elements via any known method. For example, first and/or second element 115 and/or 125 may be interchangeable at power supply 150 via extraction of electrical connector 145 coupled to first or second element 115 or 125 from power supply 150 and insertion of another electrical connector compatible with power supply 150 (not shown) electrically coupled to another element (not shown) into power supply 150. In this way, for example, micro-scissors element 115/125 as depicted in FIG. 2A (described below) may be interchanged with suction cannula element 115/125 as depicted in FIG. 2D (described below). Additionally or alternatively, surgical components 115 and/or 125 may be interchangeable with other surgical components via any conventionally available means, including, but not limited to, unscrewing or otherwise decoupling surgical component 115 and/or 125 from first and/or second elements 110 and 120. For example, a surgical component 115 or 125 may be removed from element 110 or 120, respectively, and another surgical element may be attached to the first or second element 110 or 120.

Figure 2B:
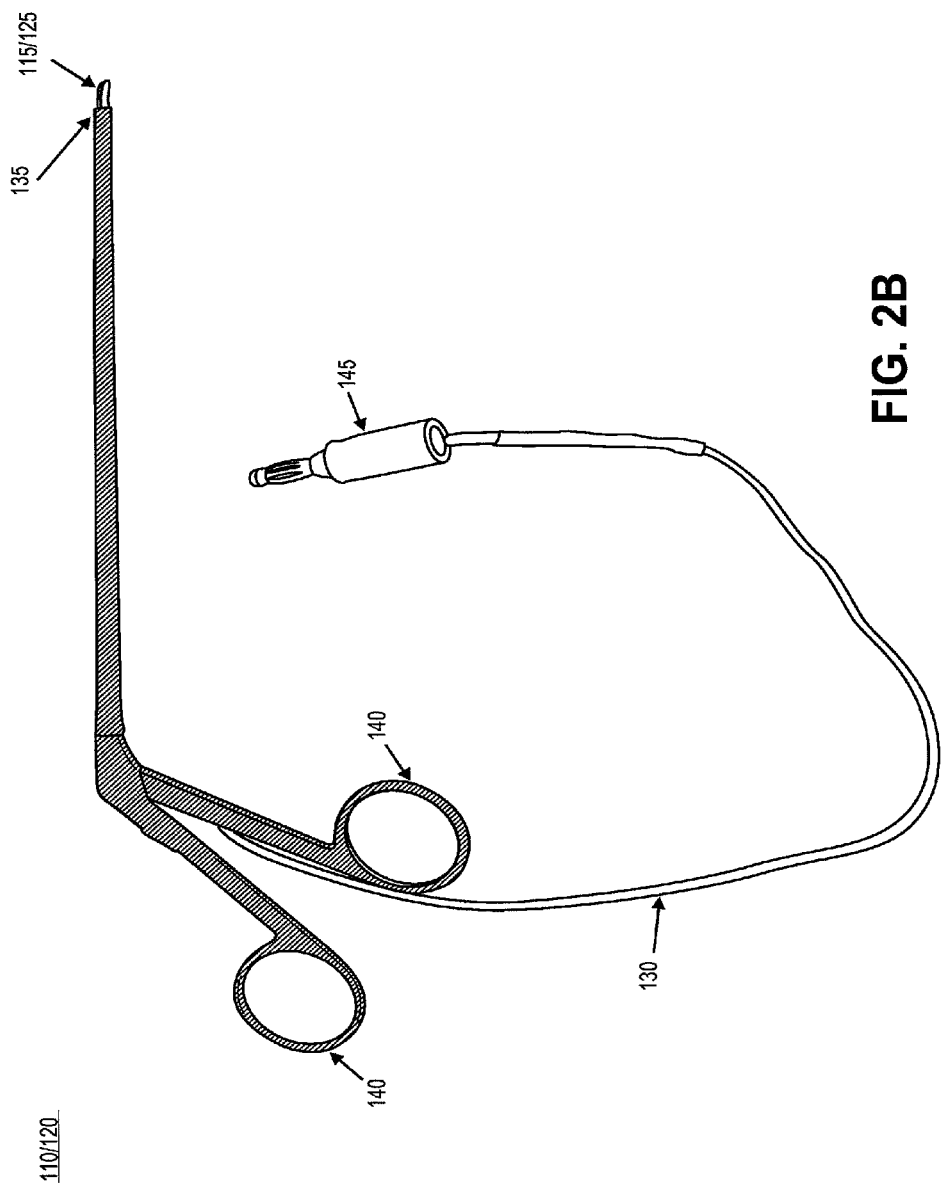
Figure 2D:
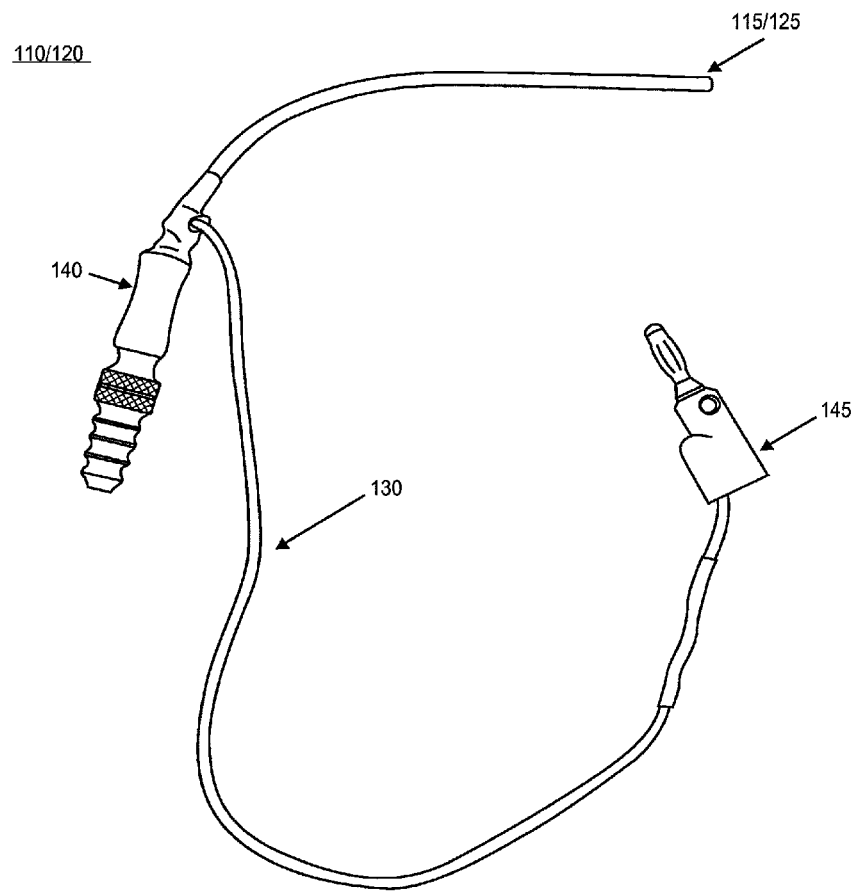
Figure 2E:
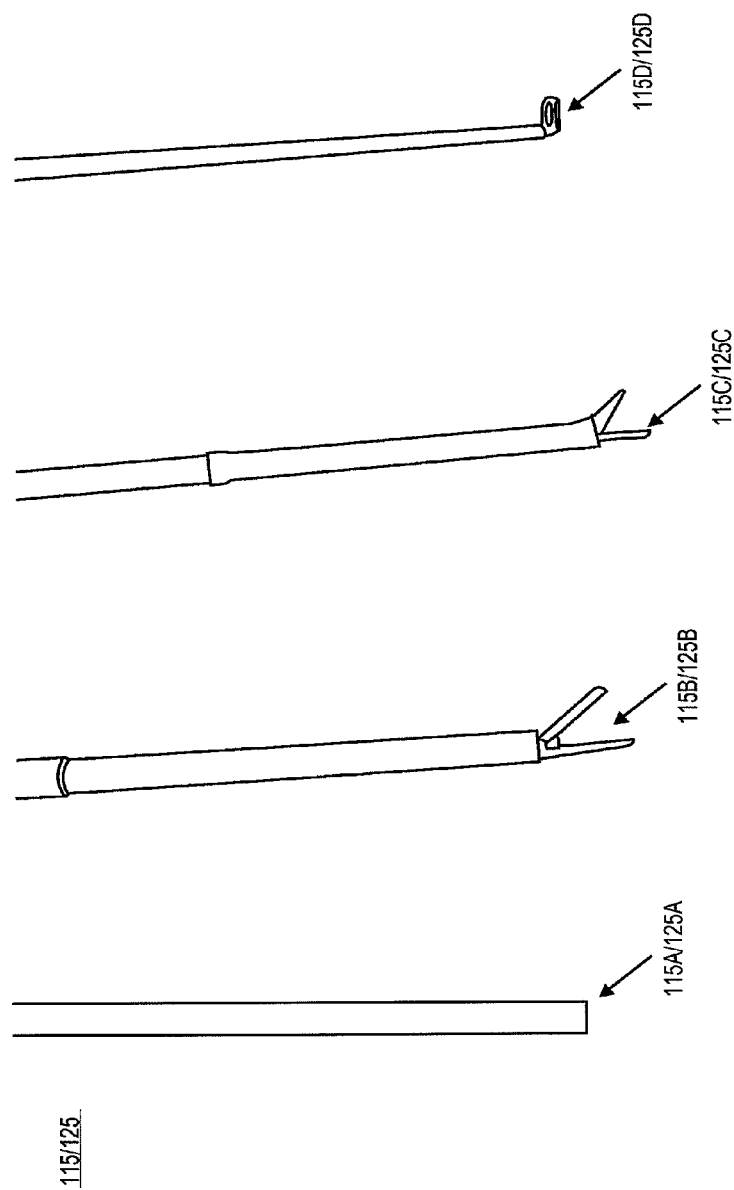
FIG. 2E depicts various exemplary surgical components, consistent with embodiments of the present invention.

FIGS. 2A-2D depict exemplary first and/or second elements 110/120. In FIG. 2A, first and/or second element 110/120 is configured as a micro-scissors tool, wherein graspers 140 are embodied as scissor handles, the shaft of the micro-scissors tool is encased in insulation 135 and surgical component 115/125 is an electrically conductive set of micro-scissors. In FIG. 2B, first and/or second element 110/120 is also configured as a micro-scissors tool, wherein the entire first and/or second element 110/120, with the exception of surgical component 115/125, is covered with insulation 135. In FIG. 2C, first and/or second element 110/120 is configured as a probe, wherein surgical component 115/125 is a surgical probe. The first and/or second element 110/120 of FIG. 2C may also include a handle 170. In FIG. 2D, first and/or second element 110/120 is configured as a suction tool, wherein surgical component 115/125 is a suction cannula. FIG. 2E depicts various exemplary surgical components 115/125, wherein surgical component 115A/125A is a suction cannula, surgical component 115B/125B is a grasper, surgical component 115C/125C is a set of micro-scissors, and surgical component 115D/125D is a probe.

Figure 3A:
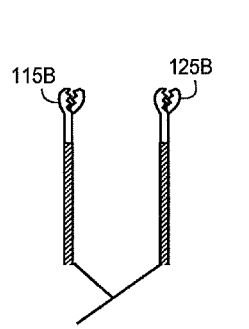
FIGS. 3A-3C depict various exemplary sets of surgical components, consistent with embodiments of the present invention.
Figure 3B:
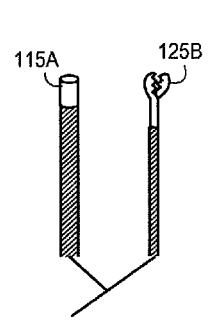
Figure 3C:
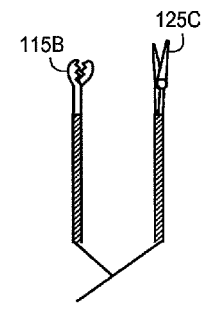

In some embodiments, first and second surgical components may be similar to, or different from, one another. For example, FIGS. 3A-3C depict various exemplary sets of surgical components 115 and 125 as provided by various embodiments of the present invention. As depicted in FIG. 3A, first and second surgical components 115B and 125B are configured as grasping elements that enable a surgeon to grasp and manipulate target tissue as well as cauterize the target tissue. As depicted in FIGS. 3B and 3C, surgical components 115 and 125 are configured differently from one another. In the embodiment depicted in FIG. 3B, surgical component 115A is configured as a suction device and surgical component 115B is configured as a grasping component. A surgeon utilizing first and second elements 110 and 120 of this embodiment would thus be enabled to grasp target tissue, suck material (e.g., blood, bone, and/or target tissue) from the patient, and cauterize target tissue while, for example, suctioning smoke resulting from cauterization to improve visualization. In the embodiment depicted in FIG. 3C, surgical component 115B is configured as a grasping tool and surgical component 115C is configured as a micro-scissors tool. A surgeon utilizing first and second elements 110 and 120 of this embodiment would thus be enabled to grasp, cut, and cauterize target tissue without requiring removal or insertion of any additional devices.

Figure 4:
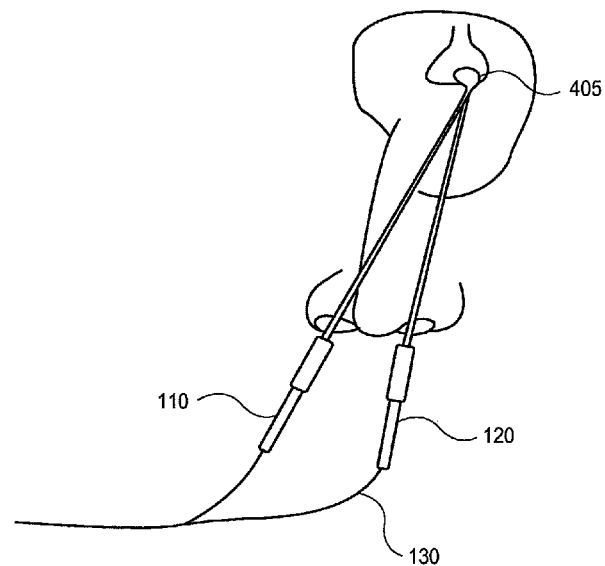
FIG. 4 illustrates an exemplary use of first and second elements, consistent with embodiments of the present invention.

FIG. 4 illustrates an exemplary use of first and second elements 110 and 120 following insertion into two ports of a patient to contact target tissue 405. In this embodiment, first element 110 is inserted into a first port within the right nostril of a patient and second element 120 is inserted into a second port within the left nostril of the patient. In this way, first and second elements may approach target tissue 405 from different angles and may move independently of one another. Following insertion of first and second elements 110 and 120 into the first and second ports within the patient, the delivery of electricity may be initiated via user selection of activation device 160 of power supply 150 thereby forming an electrical circuit. Following activation, electrical power may be delivered to first and/or second elements 110 and/or 120 and, upon contact of surgical components 115 and 125 with target tissue, electrical energy 165 may be delivered to the target tissue, thereby cauterizing the target tissue. The same application could be used for multi-port surgery in the abdomen, thorax, or any other surgical site where one or multiple access ports or corridors are utilized.

Hence, an endoscopic multi-port bipolar cautery device, system, and method of use have been herein described.

What is claimed is:

1. A surgical method, comprising:
    delivering a first electrically conductive surgical component into a patient to a target tissue site, wherein the first electrically conductive surgical component is configured to deliver electrical energy from an energy source to the target tissue site;
    delivering a second electrically conductive surgical component into the patient to the target tissue site, wherein the second electrically conductive surgical component is configured to deliver the electrical energy from the energy source to the target tissue site, wherein the second electrically conductive surgical component is positioned independently of the first electrically conductive surgical component, and when both the first and the second electrically conductive surgical components are positioned within the patient, the first and the second electrically conductive surgical components are provided at distal ends of first and second elements, respectively, that extend linearly straight from outside of the patient to the target tissue site inside of the patient, and wherein the first and the second elements are capable of being positioned at a plurality of different angles with respect to each other;
    delivering the electrical energy from the energy source between the first and the second electrically conductive surgical components to cauterize tissue at the target tissue site positioned between and contacting the first and the second electrically conductive surgical components, the delivering the electrical energy occurring while the first and the second electrically conductive surgical components are positioned at the target tissue site and both the first and the second electrically conductive surgical components are electrically coupled to the energy source; and
    using the first electrically conductive surgical component to apply suctioning to the target tissue site or to cut the tissue at the target tissue site using scissors;
    wherein the first and the second electrically conductive surgical components are inserted into nostrils of the patient.

2. The surgical method of claim 1, wherein the second electrically conductive surgical component is an electrically conductive grasper component provided at the distal end of the second element, and further comprising grasping the tissue at the target tissue site with the electrically conductive grasper component.

3. The surgical method of claim 1, wherein the first electrically conductive surgical component is an electrically conductive suction component provided at the distal end of the first element, and further comprising applying the suctioning to the target tissue site with the electrically conductive suction component.

4. The surgical method of claim 1, wherein the first electrically conductive surgical component is an electrically conductive micro-scissors component provided at the distal end of the first element, and further comprising the cutting the tissue at the target tissue site with the electrically conductive micro-scissors component.

5. The surgical method of claim 1, wherein the second electrically conductive surgical component is an electrically conductive dissection tool provided at the distal end of the second element, and further comprising dissecting the tissue at the target tissue site with the electrically conductive dissection tool.

6. The surgical method of claim 1, wherein the first electrically conductive surgical component is an electrically conductive suction component provided at the distal end of the first element and the second electrically conductive surgical component is an electrically conductive micro-scissors component provided at the distal end of the second element, and further comprising applying the suctioning to the target tissue site with the electrically conductive suction component and the cutting the tissue at the target tissue site with the electrically conductive micro-scissors component.

7. The surgical method of claim 1, wherein using the first electrically conductive surgical component to apply the suctioning to the target tissue site or to cut the tissue at the target tissue site using scissors is performed simultaneously while the delivering the electrical energy from the energy source between the first and the second electrically conductive surgical components to cauterize the tissue at the target tissue site.

8. The surgical method of claim 1, wherein the first electrically conductive surgical component is an electrically conductive micro-scissors component provided at the distal end of the first element, and further comprising the cutting the tissue at the target tissue site with the electrically conductive micro-scissors component simultaneously with delivering the electrical energy from the energy source between the first and the second electrically conductive surgical components to cauterize the tissue at the target tissue site.

9. The surgical method of claim 1, wherein the second electrically conductive surgical component is an electrically conductive grasper component provided at the distal end of the second element, and further comprising grasping the tissue at the target tissue site with the electrically conductive grasper component simultaneously with delivering the electrical energy from the energy source between the first and the second electrically conductive surgical components to cauterize the tissue at the target tissue site.

10. The surgical method of claim 1, wherein the first electrically conductive surgical component is an electrically conductive suction component provided at the distal end of the first element, and further comprising providing the suctioning to the target tissue site with the electrically conductive suction component simultaneously with delivering the electrical energy from the energy source between the first and the second electrically conductive surgical components to cauterize the tissue at the target tissue site.

11. The surgical method of claim 1, wherein the first electrically conductive surgical component and the second electrically conductive surgical component are delivered into the patient through at least one endoscopic or microsurgery port.

12. The surgical method of claim 1, wherein the first electrically conductive surgical component is inserted through a first endoscopic or microsurgery port and the second electrically conductive surgical component is inserted through a second endoscopic or microsurgery port separate and spaced apart from the first endoscopic or microsurgery port.

13. The surgical method of claim 1, wherein the first and the second electrically conductive surgical components are manipulated within the patient by a robot.

14. A surgical method, comprising:
delivering a first electrically conductive surgical component into a patient to a target tissue site, wherein the first electrically conductive surgical component is configured to deliver electrical energy from an energy source to the target tissue site;
delivering a second electrically conductive surgical component into the patient to the target tissue site, wherein the second electrically conductive surgical component is configured to deliver the electrical energy from the energy source to the target tissue site, wherein the second electrically conductive surgical component is positioned independently of the first electrically conductive surgical component, and when both the first and the second electrically conductive surgical components are positioned within the patient, the first and the second electrically conductive surgical components are provided at distal ends of first and second elements, respectively, that extend linearly straight from outside of the patient to the target tissue site inside of the patient, and wherein the first and the second elements are capable of being positioned at a plurality of different angles with respect to each other;
delivering the electrical energy from the energy source between the first and the second electrically conductive surgical components to cauterize tissue at the target tissue site positioned between and contacting the first and the second electrically conductive surgical components, the delivering the electrical energy occurring while the first and the second electrically conductive surgical components are positioned at the target tissue site and both the first and the second electrically conductive surgical components are electrically coupled to the energy source; and
using the first electrically conductive surgical component to apply suctioning to the target tissue site or to cut the tissue at the target tissue site using scissors;
wherein the first and the second electrically conductive surgical components are delivered to a skull base tumor.

15. A surgical method, comprising:
delivering a first surgical component into a patient to a target tissue site, wherein the first surgical component is configured to deliver electrical energy from an energy source to the target tissue site;
delivering a second surgical component into the patient to the target tissue site, wherein the second surgical component is configured to deliver the electrical energy from the energy source to the target tissue site, wherein the second surgical component is positioned independently of the first surgical component, and when both the first and the second surgical components are positioned within the patient, the first and the second surgical components are provided at distal ends of first and second elements, respectively, that extend linearly straight from outside of the patient to the target tissue site inside of the patient, and wherein the first and the second elements are capable of being positioned at a plurality of different angles with respect to each other;
performing a procedure comprising delivering the electrical energy at the target tissue site using the first and the second surgical components while both the first and the second surgical components are electrically coupled to the energy source;
interchanging at least the first surgical component for a third surgical component, wherein the third surgical component is configured to deliver the electrical energy from the energy source to the target tissue site; and
performing an additional function other than delivering the electrical energy from the energy source using the third surgical component while the third surgical component is electrically coupled to the energy source.

16. The surgical method of claim 15, wherein the additional function performed by the third surgical component is selected from the group consisting of grasping, suction and cutting.

17. The surgical method of claim 15, wherein the procedure comprises delivering the electrical energy between the first and the second surgical components to cauterize tissue at the target tissue site positioned between and contacting the first and the second surgical components.

18. The surgical method of claim 17, wherein the procedure further comprises performing an additional function in addition to delivering the electrical energy with the at least one of the first and the second surgical components, wherein the additional function performed with at least one of the first and the second surgical components is different from the additional function performed using the third surgical component.

19. The surgical method of claim 18, wherein the additional function performed by the at least one of the first and the second surgical components is selected from the group consisting of grasping, suction, cutting and dissection.

20. The surgical method of claim 15, wherein when both the second and the third surgical components are positioned within the patient, further comprising delivering the electrical energy between the second and the third surgical components to cauterize tissue at the target tissue site positioned between and contacting the second and third surgical components.

21. The surgical method of claim 15, wherein interchanging at least the first surgical component for the third surgical component comprises extracting an electrical connector of the first surgical component from the energy source and coupling the third surgical component to the power supply via a third electrical connector.

22. The surgical method of claim 15, wherein interchanging at least the first surgical component for the third surgical component comprises removing the first surgical component from the first element and attaching the third surgical component to the first element.

\* \* \* \* \*